(12) United States Patent
Baid (10) Patent No.: US 10,058,683 B2
(45) Date of Patent: Aug. 28, 2018

(54) CATHETER APPARATUS

(75) Inventor: Rishi Baid, New Delhi (IN)

(73) Assignee: POLY MEDICURE LIMITED, Faridabad (IN)

( * ) Notice: Subject to any disclaimer, the term of this patent is extended or adjusted under 35 U.S.C. 154(b) by 69 days.

(21) Appl. No.: 13/639,647

(22) PCT Filed: May 20, 2010

(86) PCT No.: PCT/IB2010/052239
§ 371 (c)(1),
(2), (4) Date: Oct. 5, 2012

(87) PCT Pub. No.: WO2011/154767
PCT Pub. Date: Dec. 15, 2011

(65) Prior Publication Data
US 2013/0030391 A1 Jan. 31, 2013

(30) Foreign Application Priority Data

Apr. 16, 2010 (IN) .............................. 917/DEL/2010

(51) Int. Cl.
*A61M 5/32* (2006.01)
*A61M 25/06* (2006.01)
*A61B 17/34* (2006.01)

(52) U.S. Cl.
CPC ..... *A61M 25/0618* (2013.01); *A61B 17/3496* (2013.01); *A61M 5/3273* (2013.01); *A61M 25/0631* (2013.01); *A61M 2005/325* (2013.01)

(58) Field of Classification Search
CPC ............ A61M 25/0631; A61M 5/3273; A61M 2005/325; A61M 25/0693;

(Continued)

(56) References Cited

U.S. PATENT DOCUMENTS 4,964,854 A * 10/1990 Luther ..................... 604/166.01
5,127,905 A * 7/1992 Lemieux ............... A61M 39/28
604/167.01

(Continued)

FOREIGN PATENT DOCUMENTS

| EP | 2127692 A1 * | 12/2009 | .......... A61M 5/3273 |
| WO | 03/011381 A1 | 8/2003 | |
| WO | WO 2009010847 A2 * | 1/2009 | .......... A61M 5/3273 |

OTHER PUBLICATIONS

International Search Report for PCT/IB2010/052239 dated Nov. 3, 2010.

*Primary Examiner* — Andrew Gilbert
*Assistant Examiner* — William Frehe
(74) *Attorney, Agent, or Firm* — Bodi Law LLC (57) ABSTRACT

The invention relates to a catheter apparatus comprising: a catheter; a catheter hub having a distal section and a proximal section, wherein the distal section is joined to the catheter and the proximal section defines a chamber; a needle extending through the catheter hub and the catheter and defining an axial direction, wherein the needle has opposite proximal and distal ends, the distal end forming a needle tip; a needle hub attached to the proximal end of the needle; and a needle guard slidably arranged on the needle, wherein the needle guard is retained in the chamber of the catheter hub when the needle extends through the catheter hub and the catheter, and wherein the needle guard is removable from the catheter hub once the needle tip is received in the needle guard upon withdrawal of the needle from the catheter.

22 Claims, 6 Drawing Sheets

(58) Field of Classification Search
CPC ............ A61M 25/0606; A61M 25/007; A61M 2005/3249; A61M 25/0618; A61B 17/3417; A61B 17/3401; A61B 17/3496; A61B 17/3474
USPC .......... 604/164.07–164.09, 158–163
See application file for complete search history.

(56) References Cited

U.S. PATENT DOCUMENTS

| | | | | |
|---|---|---|---|---|
| 5,279,591 | A * | 1/1994 | Simon | A61M 5/3243 604/192 |
| 5,344,408 | A * | 9/1994 | Partika | 604/192 |
| 5,558,651 | A * | 9/1996 | Crawford et al. | 604/263 |
| 5,718,688 | A * | 2/1998 | Wozencroft | A61M 5/3273 604/164.07 |
| 5,951,515 | A * | 9/1999 | Osterlind | 604/110 |
| 6,213,978 | B1 * | 4/2001 | Voyten | A61M 25/0606 604/164.01 |
| 6,565,542 | B2 * | 5/2003 | Kumar | A61B 17/3401 604/104 |
| 6,616,630 | B1 * | 9/2003 | Woehr et al. | 604/110 |
| 7,112,191 | B2 * | 9/2006 | Daga | 604/263 |
| 8,337,471 | B2 * | 12/2012 | Baid | A61M 5/3273 604/263 |
| 2002/0169418 | A1 * | 11/2002 | Menzi et al. | 604/164.07 |
| 2004/0225260 | A1 * | 11/2004 | Villa et al. | 604/164.01 |
| 2007/0179447 | A1 | 8/2007 | Carrez et al. | |
| 2007/0191774 | A1 | 8/2007 | Carrez et al. | |
| 2009/0088696 | A1 | 4/2009 | Harding et al. | |
| 2012/0277679 | A1 * | 11/2012 | Steube | A61M 25/0618 604/164.08 |

* cited by examiner

CATHETER APPARATUS

This application is a national stage application of PCT/IB2010/052239, filed May 20, 2010, which claims priority to IN Pat. No. 917/DEL/2010, filed Apr. 16, 2010, the entire contents and disclosures of which is hereby incorporated by reference.

The present invention relates to a catheter apparatus comprising a catheter; a catheter hub having a distal section and a proximal section, wherein the distal section is joined to the catheter and the proximal section defines a chamber; a needle extending through the catheter hub and the catheter and defining an axial direction, wherein the needle has opposite proximal and distal ends, the distal end forming a needle tip; a needle hub attached to the proximal end of the needle; and a needle guard slidably arranged on the needle, wherein the needle guard is retained in the chamber of the catheter hub when the needle extends through the catheter hub and the catheter, and wherein the needle guard is removable from the catheter hub once the needle tip is received in the needle guard upon withdrawal of the needle from the catheter.

As used herein, the term proximal refers to a location on the device closest to, for example, a clinician using the device. Conversely, the term distal refers to a location on the device farthest from the clinician, such as the distal needle tip to be inserted into a patient's vein.

A catheter apparatus of the above kind is generally known and typically used to facilitate insertion and placement of a catheter or another medical device into a patients vasculature.

EP 2127692 A1 discloses a catheter apparatus. WO 03/01181 teaches a catheter introducer having a needle guard which is attached to a catheter hub by means of bendable fins.

Due to the increasing incidence of blood born pathogens such as human immunodeficiency virus (HIV), hepatitis B virus (HBV) and hepatitis C virus (HCV) there is a need to protect clinicians or other medical professionals or personnel handling catheter apparatuses from accidental contact with the sharp needle tip after withdrawal of the needle from the catheter and catheter hub.

It is an object of the invention to provide a catheter apparatus which can be manufactured at a low cost and all the same provides reliable protection against accidental pricking by the needle once the needle has been withdrawn from the catheter and catheter hub.

This object is satisfied by a catheter apparatus having the features of claim 1.

The catheter apparatus of the invention comprises a catheter; a catheter hub having a distal section and a proximal section, wherein the distal section is joined to the catheter and the proximal section defines a chamber; a needle extending through the catheter hub and the catheter and defining an axial direction, wherein the needle has opposite proximal and distal ends, the distal end forming a needle tip; a needle hub attached to the proximal end of the needle; and a needle guard slidably arranged on the needle, wherein the needle guard is retained in the chamber of the catheter hub by means of a retaining arm engaging the outside of the catheter hub when the needle extends through the catheter hub and the catheter, and wherein the needle guard is removable from the catheter hub once the needle tip is received in the needle guard upon withdrawal of the needle from the catheter.

The needle guard is operative as a protector for the needle tip by automatically covering the needle tip during withdrawal of the needle from the catheter. The needle guard thereby serves to prevent accidental pricking of, for example, a clinician by the needle tip after removal of the needle from the catheter. Hence, the needle can be safely disposed of after use.

According to the invention, the retaining arm extends not parallel to the axial direction but forms an angle in the range between 00 and 10° with the axial direction such that a clearing between the retaining arm and the catheter hub narrows towards a distal end of the retaining arm. This angled orientation of the retaining arm helps the retaining arm to act as a spring arm, thereby improving the retaining effect of the retaining arm.

Securing the needle guard in the chamber of the catheter hub by means of a retaining arm engaging the outside of the catheter hub is a simple measure achieving a safe seat of the needle guard in the chamber of the catheter hub and thus effectively preventing accidental removal of the needle guard from the catheter chamber prior to the needle tip being received in the needle guard. Hence, the catheter apparatus of the invention can be manufactured at reduced costs while at the same time the safety of the catheter apparatus is increased.

According to an embodiment, a proximal end of the retaining arm is connected to a base portion of the needle guard by means of a transverse segment. The transverse segment may extend generally in a radial direction, i.e. perpendicular to the axial direction defined by the needle. Preferably, the transverse segment extends from a proximal end region of the needle guard.

In order to further increase the retaining effect of the retaining arm, a hook-like protrusion may be provided in the region of a distal end of the retaining arm.

The retaining effect may be increased even more, if a projection or a recess or a combination of a projection and a recess is provided on the outer surface of the catheter hub for engagement with the retaining arm, in particular for engagement with a hook-like protrusion provided in the region of a distal end of the retaining arm.

According to another embodiment, at least one supporting arm for engaging the outer surface of the catheter hub is provided on a side of the needle guard opposite from the retaining arm. The supporting arm helps to prevent the needle guard received in the catheter hub from moving in a radial direction within the chamber. In other words, the supporting arm stabilizes the needle guard in the catheter hub and thus adds to a desired positioning of the needle guard in the chamber. The supporting arm may or may not be in a retaining relationship with the catheter hub.

According to still another embodiment, the needle guard comprises a generally cylindrical base portion in the region of its proximal end as well as first and second arms extending in a generally axial direction from a distal side of the base portion, wherein the first and second arms are surrounded by a tension element, e.g. an elastic band, in a distal region of the first and second arms.

The tension element exerts a restoring force on the first and second arms when the first and second arms are spread apart by the needle extending all the way through the needle guard, which is the state in which the catheter apparatus is typically shelved prior to use. The tension element thus ensures that the spread apart arms will snap together and guard the needle tip upon withdrawal of the needle from the catheter even after a longer shelf time, thereby continuously ensuring a correct functioning of the needle guard. In addition, the tension element prevents the arms from becoming loose when the needle safety device slides along the needle, thereby further adding to a correct functioning of the needle safety device. Furthermore, the tension element helps prevent the needle tip from protruding sideways out of the needle guard, thereby further increasing the protective function of the needle safety device.

Preferably, the first and second arms are spread apart by the needle extending completely through the needle guard such that the tension element is brought into retaining engagement with an inner surface of the catheter hub. This adds to the retaining effect achieved by the retaining arm and further increases the safety of the apparatus. The inner surface of the catheter hub, in particular the inner surface confining the chamber, may be generally smooth.

In order to prevent the needle tip received in the needle guard from distally protruding from the needle guard, a transverse wall may be arranged in a distal region of one of the first and second arms with a groove provided in a side of the transverse wall, the groove extending substantially in the axial direction. The groove acts as a guide groove for the needle and aids the axial movement of the needle relative to the needle guard. Moreover, the needle is prevented from sliding sideways off the transverse wall. Such a sideways movement would significantly increase the force required to move the needle relative to the needle guard, which would prevent a correct functioning of the needle guard.

According to a further embodiment, a recess is formed in said one of the first and second arms, i.e. in the arm carrying the transverse wall. Preferably, the recess is formed on the outside of the arm and/or in a region between the base portion and the tension element. The recess increases the deflectability of the arm in the region it is provided and thereby reduces the restoring force acting on the transverse wall while this is being supported by the needle. This allows the needle to be moved more easily relative to the transverse wall, as the frictional force acting on the needle is reduced. The recess may, for example, be formed by a groove extending in a direction transverse to both the axial direction and the radial direction.

The catheter apparatus is particularly inexpensive to manufacture if the base portion, the first and second arms, the retaining arm and the supporting arm are integrally made from a first material. The first material may, for example, be a plastic material. Thus the base portion, the first and second arms, the retaining arm and the supporting arm could be manufactured by injection molding.

Alternatively, the base portion, one of the first and second arms and the retaining arm could be integrally made from a first material, e.g. a plastic material, and the other one of the first and second arms could be made from a second material different from said first material. For example, said other one of the first and second arms could include a strip of material having spring-like properties, e.g. a strip of sheet metal.

According to another embodiment, the base portion of the needle guard has an axial bore extending therethrough for receiving the needle, wherein the profile of the bore is adapted to the principal outer profile of the needle, and the needle has a change in profile, in particular an enlargement, near the needle tip, said change in profile having an outer profile one dimension of which is larger than a maximum dimension of the profile of the bore. The change in profile prevents the needle guard from sliding off the needle when the needle tip is received between the arms, thereby further improving the protective function of the needle safety device.

The change in profile may, for example, be made by a crimping of the needle. However, other ways of forming the change in profile are possible, e.g. by subjecting the needle to concentrated heat at a localized area using, for example, a welding process such as a laser welding process without addition of additional material. Alternatively, the change in profile may be formed from additional material dispensed onto the outer surface of the needle. In order to locate the dispensed material in a defined position, a recess or groove may be formed in the outer surface or circumference of the needle. The additional material may, for example, be selected from at least one of a plastic material, an adhesive, a resin and a metal material. In the case of the additional material being a metal material, the change in profile may, for example, be formed by build-up welding or by soldering of the additional material onto the needle. Alternatively, the additional material could be glued to the needle.

The inner profile of the needle can either be reduced in the region of the change in profile, for example, if the change in profile is formed by crimping, or it can be substantially constant throughout the length of the needle, for example, if the change in profile is formed by applying additional material to the needle.

According to still another embodiment, the base portion of the needle guard is made from a first material and has an axial bore extending therethrough for receiving the needle, and a stopping element is provided in the base portion or on a distal or proximal side thereof, the stopping element being made of a second material different from the first material and having a through-bore which is aligned with the axial bore and has a profile that is adapted to a principal outer profile of the needle, wherein the needle has a change in profile near the needle tip, said change in profile having an outer profile one dimension of which is larger than a maximum dimension of the profile of the bore.

Preferably, the second material is of a greater hardness and/or stiffness than the first material. For example, the first material could be a plastic material and the second material could consist of a metal, a ceramic or a rubber material, or any other type of material which is stiff and not as easily distorted as the first material.

Furthermore, the stopping element can be a circular disk, a ring, or a washer. However, it need not necessarily be circular and can have any other geometric shape such as a rectangular, square or triangular shape.

Alternatively, the stopping element may be defined by one of the first and second arms, in particular from a proximal end portion of said arm, said arm preferably being formed from a strip of sheet metal. This embodiment is particularly advantageous, since said arm thus fulfills a double function in that it not only protects the needle tip from protruding distally from the needle guard but also helps to prevent the needle guard from sliding off the needle.

Preferred embodiments of the invention are described in the following description and in the accompanying drawings, wherein.

Figure 1A:
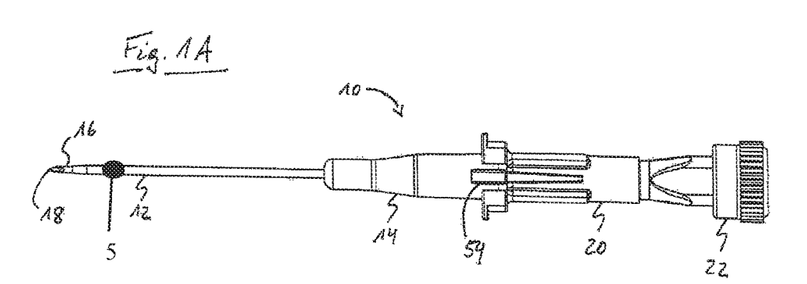
FIGS. 1A and B show side views of a catheter apparatus of the invention prior to use.
Figure 1B:
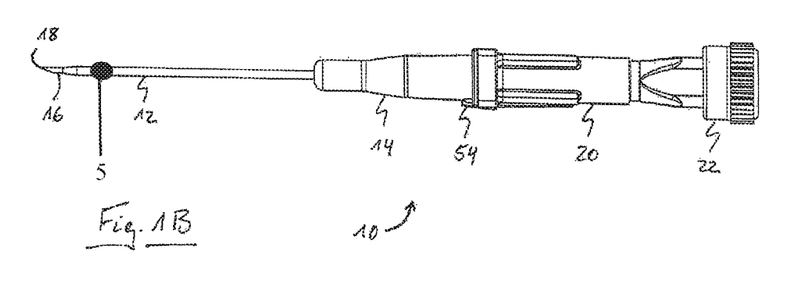

FIG. 1 shows a catheter apparatus 10 in accordance with the invention prior to use. The catheter apparatus 10 includes a tube-like catheter 12 having distal and proximal ends, and a catheter hub 14 attached to the catheter 12 at the proximal end of the catheter 12.

The catheter apparatus 10 further comprises a needle 16 extending through the catheter 12 and catheter hub 14 and defining an axial direction. The needle 16 has distal and proximal ends, wherein a sharp needle tip 18 is formed at the distal end of the needle 16, which protrudes from the catheter 12 at the distal end thereof.

A needle hub 20 is attached to the needle 16 at the proximal end of the needle 16. A port member 22 is mounted to the needle hub 20 at a proximal side of the needle hub 20, which makes it possible to connect, for example, a PVC tube to the catheter apparatus 10 for collecting blood from a patient or delivering a fluid to be administered to a patient.

The catheter hub 14 defines an inner chamber (FIG. 4) in which a needle guard 26 is seated. In FIG. 1 only a retaining arm 54 of the needle guard 26 can be seen. The needle guard 26 is slidably arranged on the needle 16, such that it moves along the needle 16 when the needle 16 is withdrawn from the catheter 12. The purpose of the needle guard 26 is to cover the needle tip 18 after the needle 16 has been used in order to prevent accidental pricking by the needle 16 of a person handling the catheter apparatus 10, as can be seen from FIG. 2.

Figure 3A:
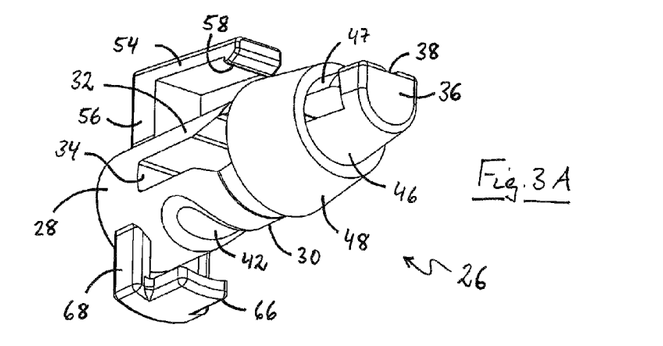
FIGS. 3A to C show perspective views (A and B) and a side view (C) of the needle guard of FIG. 2.
Figure 3B:
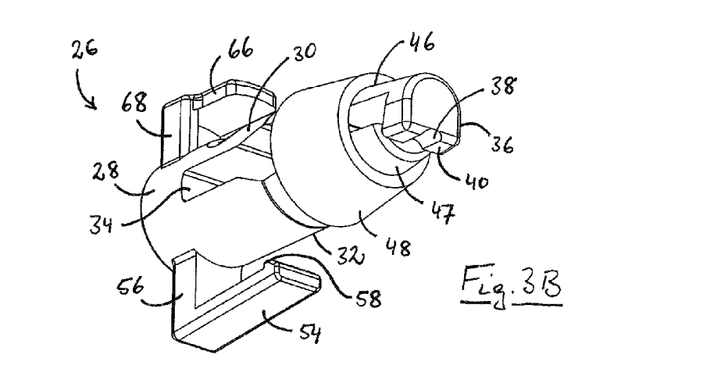
Figure 3C:
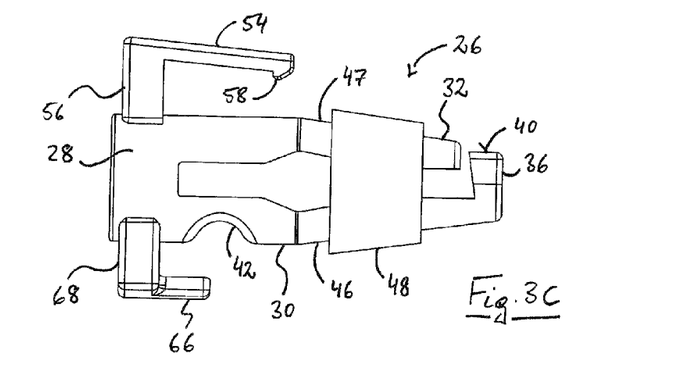

As shown in FIG. 3, the needle guard 26 includes a generally cylindrical base portion 28 at a proximal end of the needle guard 26. First and second arms 30, 32 extend from a distal face 34 of the base portion 28 generally in the axial direction. The first arm 30 is longer than the second arm 32.

Figure 2:
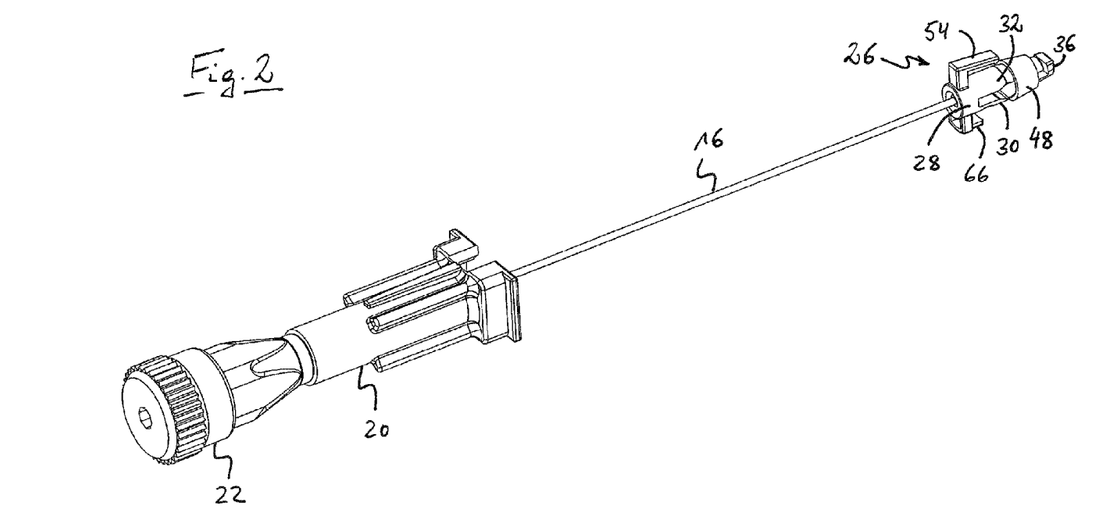
FIG. 2 shows a perspective view of a needle, a needle hub attached thereto and a needle guard guarding a tip of the needle after use of the catheter apparatus of FIG. 1.

A transverse wall 36 is arranged in a distal region of the first arm 30. The dimension of the transverse wall 36 as seen in a radial direction is selected such that the transverse wall 36 overlaps with the second arm 32 when the needle tip 18 is received in the needle guard 26, i.e. between the first and second arms 30, 32, such that the needle tip 18 is blocked by the transverse wall 36 from distally protruding from the needle guard 26 (FIG. 2).

Prior to use, i.e. when the needle 16 extends all the way through the needle guard 26, the transverse wall 36 is supported on the needle 16 and the first arm 30 is deflected away from the second arm 32. An axial groove 38 is provided in the transverse wall 36 on its side 40 facing the needle 16 in order to guide the transverse wall 36 on the needle 16, in particular when the needle 16 is pulled through the needle guard 26 upon withdrawal of the needle 16 from the catheter 12.

A recess 42 is provided in the outer surface of a proximal section 44 of the first arm 30 in order to increase the deflectability of the first arm 30.

Figure 4:
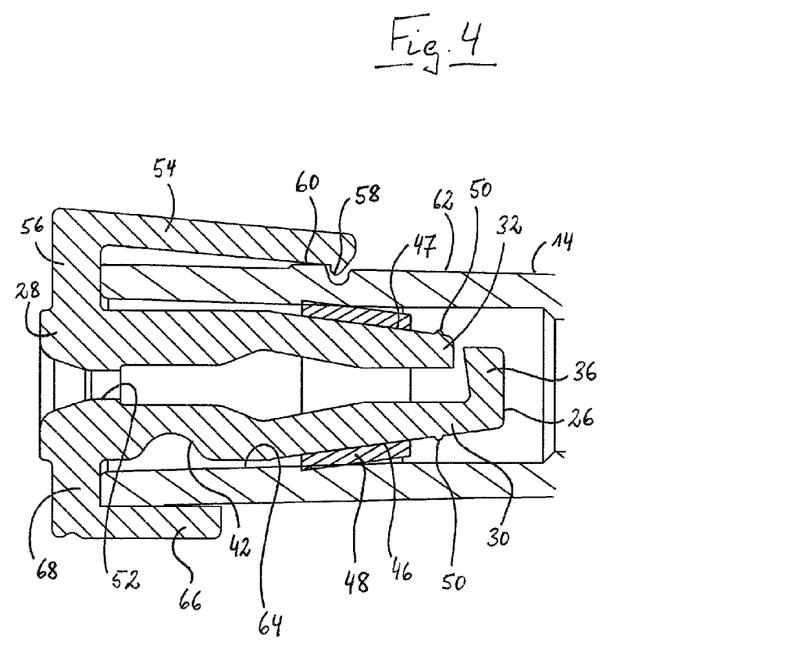
FIG. 4 shows a longitudinal sectional view of a needle guard received in a catheter hub of the catheter apparatus of FIG. 1.

Distal sections 46, 47 of the first and second arms 30, 32 have outer surfaces that are tapered towards the distal ends of the first and second arms 30, 32. The first and second arms 30, 32 are surrounded by an elastic band 48 in the region of the distal sections 46, 47. Because of the tapered outer surfaces of the distal sections 46, 47 the elastic band 48 is prevented from sliding off the distal sections 46, 47 towards the proximal end of the needle guard 26 when the first and second arms 30, 32 are spread apart against a restoring force of the elastic band 48 by the needle 16 extending all the way through the needle guard 26. In order to further define the axial position of the elastic band 48, protrusions 50 extending along the outer periphery of the first and second arms 30, 32 can be provided adjacent the elastic band 48 (FIG. 4). These protrusions 50 are not shown in FIGS. 2 and 3.

As is best seen in FIG. 4, an axial bore 52 extends through the base portion 28 of the needle guard 26 for receiving the needle 16. The profile of the bore 52 is adapted to the principle outer profile of the needle 16. The needle 16 has a change in profile 5 (see FIGS. 1a, 1b), in particular an enlargement near its needle tip 18, which has an outer profile one dimension of which is larger than a maximum dimension of the profile of the bore 52. Thus, the change in profile 5 prevents the needle guard 26 from sliding off the needle 16 when the needle tip 18 is received between the first and second arms 30, 32 and covered by the needle guard 26.

A retaining arm 54 is provided on the needle guard 26 in order to secure the needle guard 26 in the chamber of the catheter hub and, in particular, to prevent removal of the needle guard 26 from the catheter hub 14 upon withdrawal of the needle 16 before the needle tip 18 has been safely received in the needle guard 26. The retaining arm 54 is connected to the base portion 28 of the needle guard 26 via a transverse segment 56. The transverse segment 56 extends outwardly from the base portion 28 in a generally radial direction at the side of the second arm 32. The retaining arm 54 extends distally from the transverse segment 56 and is slightly tilted towards the second arm 32. Preferably, the retaining arm 54 forms an angle in the range between 0° and 10° with the axial direction, such that a clearing between the retaining arm 54 and the second arm 32 narrows towards a distal end of the retaining arm 54.

A hook-like protrusion 58 is provided in the region of the distal end of the retaining arm 54. The hook-like protrusion 58 of the retaining arm 54 engages behind a corresponding protrusion 60 and into a groove or recess provided at the outer surface 62 of the catheter hub 14. Because of the engagement between the hook-like protrusion 58 of the retaining arm 54 and the combination of protrusion 60 and recess formed on the catheter hub 14, the needle guard 26 is prevented from axial movement relative to the catheter hub 14 and effectively retained at the catheter hub 14 until a pulling force exerted by the needle 16 on the base portion 28 of the needle guard 26 via the change in profile of the needle 16 upon withdrawal of the needle 16 from the catheter 12 becomes great enough to disengage the retaining arm 54 from the protrusion 60 of the catheter hub 14.

It is to be noted that instead of a combination of protrusion 60 and recess formed at the catheter hub 14 it is also possible to provide either a protrusion 60 or a recess in the outer surface 62 of the catheter hub 14 for engagement with the hook-like protrusion 58 of the retaining arm 54.

The retaining of the needle guard 26 in the catheter hub 14 can be further improved if the elastic band 48 engages with an inner surface 64 of the catheter hub 14 in the spread-apart state of the first and second arms 30, 32. Once the needle tip 18 passes the transverse wall 36 and the first and second arms 30, 32 snap together, thereby allowing the elastic band 48 to contract, the elastic band 48 can disengage from the inner surface 64 of the catheter hub 14.

A supporting arm 66 is provided on a side of the needle guard 26 opposite from the retaining arm 54. The supporting arm 66 forms a generally right angle with a transverse segment 68 which extends from the base portion 28 in a generally radial direction. The supporting arm 66 is configured to be in contact with the outer surface 62 of the catheter hub 14 across its substantially entire length and width. The supporting arm 66 thus prevents the needle guard 26 received in the catheter hub 14 from moving in a radial direction within the chamber. The supporting arm 66 may also help to secure the needle guard 26 against axial movement with respect to the catheter hub 14, thereby adding to the retaining of the needle guard 26 in the catheter hub 14. However, the supporting arm 66 does not necessarily have to be in such a retaining relationship with the catheter hub 14.

In the present embodiment, the retaining arm 54 is provided on the side of the base portion 28 adjacent the second arm 32, and the supporting arm 66 is provided on the side of the base portion 28 adjacent the first arm 30. However, it is generally also possible to provide the retaining arm 54 on the side of the base portion 28 adjacent the first arm 30 and the supporting arm 66 on the side of the base portion 28 adjacent the second arm 32.

As shown in FIGS. 1 to 4, the base portion 28, the first and second arms 30, 32, the retaining arm 54 and the supporting arm 66 are integrally formed, for example, from a plastic material by way of injection molding. However, it is to be understood that this integral design is not compulsory. Instead, one or more of the named components could be made of a material that is different from the material of the other components, and this component could be attached to the other components, for example, by gluing, welding, soldering or the like.

Although not shown in FIGS. 1 to 4, a stopping element may be provided in the base portion 28 or on the distal face 34 of the base portion 28, wherein the stopping element has a through-bore which is aligned with the axial bore 52 in the base portion 28 and which has a profile that is adapted to the principle outer profile of the needle 16. Preferably, such a stopping element would be made of a material of a greater hardness and/or stiffness than the material of the base portion 28, such that this stopping element withstands greater forces exerted by the change in profile of the needle 16 upon withdrawal of the needle 16 from the catheter 12, thereby more effectively preventing the change in profile of the needle 16 from passing through the base portion 28 and thus more effectively preventing the needle guard 26 from sliding off the needle 16.

Figure 5A:
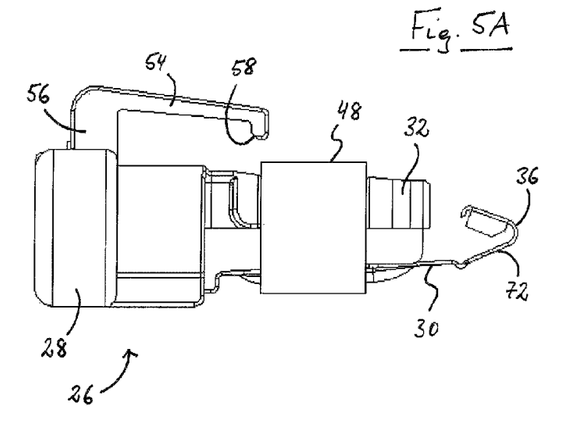
FIGS. 5A and B show a side view (A) and a perspective view (C) of an alternative needle guard.
Figure 5B:
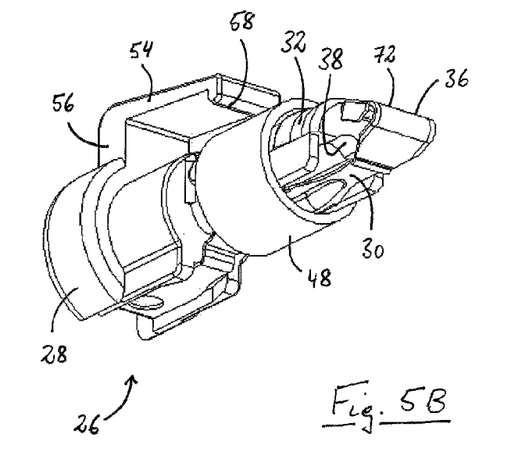
Figure 6A:
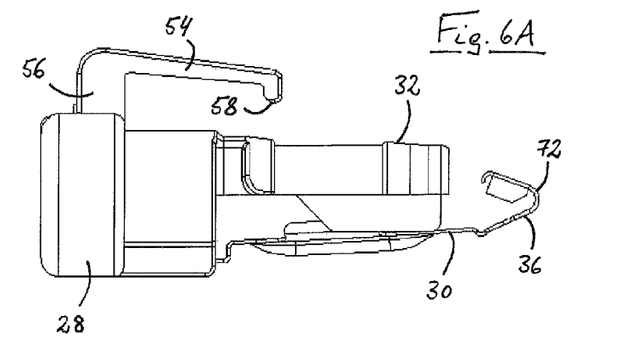
FIGS. 6A to C show a side view (A), a perspective view (B) and a longitudinal sectional view (C) of the needle guard of FIG. 5 without tension element.
Figure 6B:
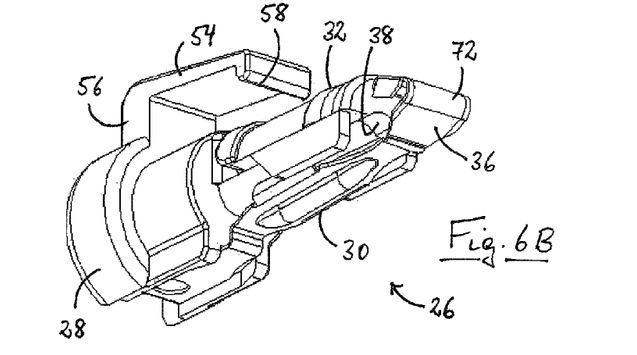
Figure 6C:
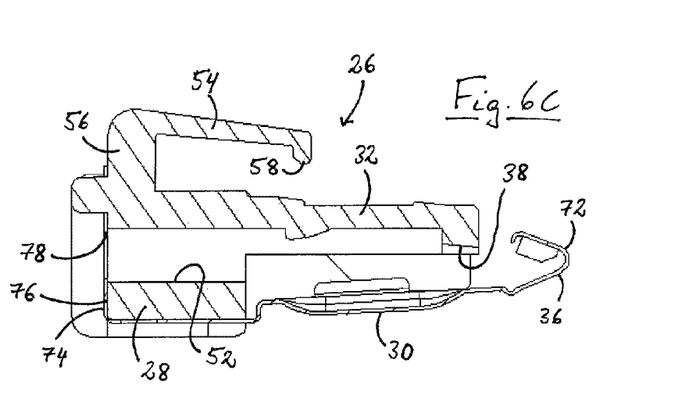

FIGS. 5 and 6 show an alternative needle guard 26 that can be used in the catheter apparatus 10 of the invention. This needle guard 26 is generally identical in function but differs from the aforedescribed needle guard 26 mainly in that it does not have any supporting arm and in that the first arm 30 is not integrally formed with the base portion 28, the second arm 32 and the retaining arm 54.

Instead, the first arm 30 is made of a strip of sheet metal, a distal end portion 72 of which is bent to form the transverse wall 36 and a proximal end portion 74 of which is attached, e.g. glued or welded, to a proximal face 76 of the base portion 28. As described above, distal sections 46, 47 of the first and second arms 30, 32 are surrounded by an elastic band 48 such that the first and second arms 30, 32 can be spread apart against a restoring force of the elastic band 48 (FIG. 5).

As is best seen in FIG. 6C, a through-bore 78 is provided in the proximal end portion 74 of the strip of sheet metal and aligned with the axial bore 52 in the base portion 28. The profile of the through-bore 78 is adapted to the principal outer profile of the needle 16, whereas the profile of the axial bore 52 is somewhat wider. Hence, in this needle guard 26 the change of profile of the needle 16, e.g. its enlargement, can slide along the axial bore 52 and is limited in movement in the proximal direction only upon engagement with the proximal end portion 74 of the strip of sheet metal at the proximal side of the base portion 28. The proximal end portion 74 of the strip of sheet metal thus functions as a stopping element of the kind that has already been discussed above and helps to prevent the needle guard 26 from sliding off the needle 16.

In further contrast to the needle guard 26 shown in FIGS. 1 to 4, in the needle guard 26 of FIGS. 5 and 6 the axial groove 38 for guiding the needle 16 upon movement relative to the needle guard 26 is not provided on the first arm 30 but on the second arm 32, as is best seen in FIG. 6B.

REFERENCE NUMERAL LIST 10 catheter apparatus
12 catheter
14 catheter hub
16 needle
18 needle tip
20 needle hub
22 port member
26 needle guard
28 base portion
30 first arm
32 second arm
34 distal face
36 transverse wall
38 axial groove
40 side
42 recess
44 proximal portion
46 distal section
47 distal section
48 elastic band
50 protrusion
52 axial bore
54 retaining arm
56 transverse segment
58 protrusion
60 protrusion
62 outer surface
64 inner surface
66 supporting arm
68 transverse segment
72 distal end portion
74 proximal end portion
76 proximal face
78 through-bore

The invention claimed is:

1. A catheter apparatus comprising:
   a catheter;
   a catheter hub having a distal section and a proximal section, wherein the distal section is joined to the catheter and the proximal section defines a chamber;
   a needle extending through the catheter hub and the catheter and defining an axial direction, wherein the needle has opposite proximal and distal ends, the distal end forming a needle tip;
   a needle hub attached to the proximal end of the needle; and
   a needle guard slidably arranged on the needle, wherein the needle guard is retained in the chamber of the catheter hub by means of a retaining arm engaging the outside of the catheter hub when the needle extends through the catheter hub and the catheter, and wherein the needle guard is removable from the catheter hub and remains with the needle to protect the needle tip once the needle tip is received in the needle guard upon withdrawal of the needle from the catheter, and wherein the needle guard comprises a generally cylindrical base portion in the region of its proximal end and first and second arms extending in a generally axial direction from a distal side of the base portion, wherein the first and second arms are at least party surrounded by a tension element in a distal region of the first and second arms, such that the first and second arms are spread apart by the needle extending completely through the needle guard such that the tension element is brought into circumferential retaining engagement with a generally smooth inner surface confining the chamber of the catheter hub.

2. A catheter apparatus in accordance with claim 1, wherein a proximal end of the retaining arm is connected to a base portion of the needle guard by means of a transverse segment, in particular wherein the transverse segment extends generally in a radial direction and/or from a proximal end region of the needle guard.

3. A catheter apparatus in accordance with claim 1, wherein a hook-like protrusion is provided in the region of a distal end of the retaining arm.

4. A catheter apparatus in accordance with claim 1, wherein a projection or a recess or a combination of a projection and a recess is provided on the outer surface of the catheter hub for engagement with the retaining arm, in particular with a hook-like protrusion provided in the region of a distal end of the retaining arm.

5. A catheter apparatus in accordance with claim 1, wherein at least one supporting arm for engaging the outer surface of the catheter hub is provided on a side of the needle guard opposite from the retaining arm.

6. A catheter apparatus in accordance with claim 1, wherein a transverse wall is arranged in a distal region of one of the first and second arms, wherein a groove is provided in a side of the transverse wall, the groove extending substantially in the axial direction.

7. A catheter apparatus in accordance with claim 1, wherein a recess is formed in said one of the first and second arms, in particular on the outside of the arm(s) and/or in a region between the base portion and the tension element.

8. A catheter apparatus in accordance with claim 1, wherein the base portion, the first and second arms, the retaining arm and, if present, a supporting arm are integrally made from a first material.

9. A catheter apparatus in accordance with claim 1, wherein the base portion, one of the first and second arms and the retaining arm are integrally made from a first material and the other one of the first and second arms is made from a second material different from said first material including a strip of material having spring-like properties.

10. A catheter apparatus in accordance with claim 9, wherein the strip of material having spring-like properties comprises a strip of sheet metal.

11. A catheter apparatus in accordance with claim 1, wherein the base portion of the needle guard has an axial bore extending therethrough for receiving the needle, wherein the profile of the bore is adapted to the principal outer profile of the needle, and the needle has a change in profile near the needle tip, said change in profile having an outer profile one dimension of which is larger than a maximum dimension of the profile of the bore, the said change in profile is formed by subjecting the needle to concentrated heat at a localized area.

12. A catheter apparatus in accordance with claim 11, wherein the profile of the needle is formed by subjecting the needle to a laser welding process.

13. A catheter apparatus in accordance with claim 1, wherein the base portion of the needle guard is made from a first material and has an axial bore extending therethrough for receiving the needle, and a stopping element is provided in the base portion or on a distal or proximal side thereof, the stopping element being made of a second material different from the first material, having a disk-like shape and/or being made as a ring or as a washer, the second material being of a greater hardness and/or stiffness than the first material, the stopping element having a through-bore which is aligned with the axial bore and has a profile that is adapted to a principal outer profile of the needle, wherein the needle has a change in profile near the needle tip, said change in profile having an outer profile one dimension of which is larger than a maximum dimension of the profile of the through-bore.

14. A catheter apparatus in accordance with claim 13, wherein the stopping element is defined by a proximal end portion of one of the first or second arms.

15. A catheter apparatus in accordance with claim 13, wherein the change in profile is formed from additional material dispensed onto the outer surface of the needle, wherein the additional material is selected from at least one of a plastic material, an adhesive, a resin and a metal material.

16. A catheter apparatus in accordance with claim 13, wherein a recess is formed by a groove extending in a direction transverse to both the axial direction and a radial direction.

17. A catheter apparatus in accordance with claim 13, wherein the first material is integrally made from a plastic material by injection molding.

18. A catheter apparatus in accordance with claim 1, wherein an arm for protecting a tip of said needle comprises a strip of sheet metal.

19. A catheter apparatus in accordance with claim 1, further comprising a tension element including an elastic band.

20. The apparatus of claim 1, wherein the retaining arm extends linearly in a direction not parallel to the axial direction and forms an angle in the range greater than 0° up to 10° with the axial direction such that a clearing between the retaining arm and the catheter hub narrows towards a distal end of the retaining arm.

21. A catheter apparatus comprising:
a catheter;
a catheter hub having a distal section and a proximal section, wherein the distal section is joined to the catheter and the proximal section defines a chamber;
a needle extending through the catheter hub and the catheter and defining an axial direction, wherein the needle has opposite proximal and distal ends, the distal end forming a needle tip;
a needle hub attached to the proximal end of the needle; and
a needle guard slidably arranged on the needle, wherein the needle guard is retained in the chamber of the catheter hub by means of a retaining arm fixedly attached to a base portion of the needle guard and having a tab extension configured to engage a depression provided on the outside of the catheter hub to engage the retaining arm and the catheter hub when the needle extends through the catheter hub and the catheter, and wherein the needle guard is removable from the catheter hub and remains with the needle to protect the needle tip once the needle tip is received in the needle guard upon withdrawal of the needle from the catheter, wherein the retaining arm extends in a direction not parallel to the axial direction and forms an angle in the range greater than 0° up to 10° with the axial direction such that a clearing between the retaining arm and the catheter hub narrows towards a distal end of the retaining arm, wherein the needle guard comprises a generally cylindrical base portion in the region of its proximal end and first and second arms extending in a generally axial direction from a distal side of the base portion, wherein the first and second arms are at least party surrounded by a tension element in a distal region of the first and second arms, such that the first and second arms are spread apart by the needle extending completely through the needle guard such that the tension element is brought into circumferential retaining engagement with a generally smooth inner surface confining the chamber of the catheter hub.

22. A catheter apparatus comprising:

a catheter;

a catheter hub having a distal section and a proximal section, wherein the distal section is joined to the catheter and the proximal section defines a chamber;

a needle extending through the catheter hub and the catheter and defining an axial direction, wherein the needle has opposite proximal and distal ends, the distal end forming a needle tip;

a needle hub attached to the proximal end of the needle; and a needle guard slidably arranged on the needle, wherein the needle guard is retained in the chamber of the catheter hub by means of a retaining arm having a proximal portion fixedly attached to a base portion of the needle guard and having a hook-like protrusion provided in the region of a distal end of the retaining arm configured for engaging a groove provided on an outer surface of the catheter hub away from a proximal portion of the catheter hub when the needle guard engages the catheter hub, and wherein the needle guard is removable from the catheter hub when the needle tip is received in the needle guard which remains with the needle to protect the needle tip upon withdrawal of the needle from the catheter, wherein the retaining arm extends linearly in a direction not parallel to the axial direction and forms an angle in the range greater than 0° up to 10° with the axial direction such that a clearing between the retaining arm and the catheter hub narrows towards a distal end of the retaining arm, wherein the needle guard comprises a generally cylindrical base portion in the region of its proximal end and first and second arms extending in a generally axial direction from a distal side of the base portion, wherein the first and second arms are at least partly surrounded by a tension element in a distal region of the first and second arms, wherein the first and second arms are spread apart by the needle extending completely through the needle guard such that the tension element is brought into circumferential retaining engagement with an inner surface confining the chamber of the catheter hub, wherein the said inner surface is generally smooth.

* * * * *